United States Patent

Shimizu et al.

[11] Patent Number: 5,578,244
[45] Date of Patent: Nov. 26, 1996

[54] SILACYCLOHEXANE COMPOUND, A METHOD OF PREPARING IT AND A LIQUID CRYSTAL COMPOSITION CONTAINING IT

[75] Inventors: Takaaki Shimizu; Takeshi Kinsho; Tsutomu Ogihara; Tatsushi Kaneko; Mutsuo Nakashima, all of Niigata-ken; Hideshi Kurihara, Kawasaki, all of Japan

[73] Assignee: Shin-Etsu Chemical Co., Ltd., Tokyo, Japan

[21] Appl. No.: 415,858

[22] Filed: Apr. 3, 1995

[30] Foreign Application Priority Data

Apr. 5, 1994 [JP] Japan .................. 6-090495
May 2, 1994 [JP] Japan .................. 6-115872
Jun. 13, 1994 [JP] Japan .................. 6-154220
Jul. 29, 1994 [JP] Japan .................. 6-197895

[51] Int. Cl.$^6$ .................. C09K 19/34; C09K 19/12; C07F 7/08; G02F 1/13
[52] U.S. Cl. .................. 252/299.61; 252/299.66; 556/406; 359/103
[58] Field of Search .................. 556/406; 252/299.61, 252/299.66

[56] References Cited

U.S. PATENT DOCUMENTS

| | | | |
|---|---|---|---|
| 2,607,791 | 8/1952 | Goodwin et al. | 556/406 X |
| 3,359,293 | 12/1967 | Wu et al. | 556/406 X |
| 5,389,295 | 2/1995 | Wachtler et al. | 252/299.63 |
| 5,454,977 | 10/1995 | Shimizu et al. | 252/299.61 |

FOREIGN PATENT DOCUMENTS

| | | |
|---|---|---|
| 0444448 | 9/1991 | European Pat. Off. . |
| 0449288 | 10/1991 | European Pat. Off. . |
| 0630903 | 12/1994 | European Pat. Off. . |
| 0632044 | 1/1995 | European Pat. Off. . |

*Primary Examiner*—C. H. Kelly
*Attorney, Agent, or Firm*—Townsend & Banta

[57] ABSTRACT

A silacyclohexane compound represented by the following general formula (I)

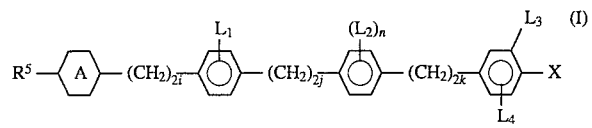

wherein R denotes a linear-chain alkyl group with a carbon number of 1–10, a fluoroalkyl group with a carbon number of 1–10 in which a fluorine atom(s) is substituted for one or two hydrogen atoms, a branched-chain alkyl group with a carbon number of 3–8, an alkoxyalkyl group with a carbon number of 2–7, or an alkenyl group with a carbon number of 2–8.

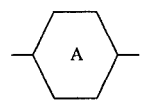

denotes a trans-1-sila-1,4-cyclohexylene or trans-4-sila-1,4-cyclohexylene group whose silicon at position 1 or position 4 has a substitutional group(s) of H, F, Cl or $CH_3$. $L_1$ and $L_2$ independently denote H or F. $L_3$ and $L_4$ independently denote H, F or Cl. X denotes a H, CN, F, Cl, $CF_3$, $CF_2Cl$, $CHFCl$, $OCF_3$, $OCF_2Cl$, $OCHFCl$, $OCHF_2$, or a linear-chain alkyl or alkoxy group with a carbon number of 1–10. i, j and k respectively denote 0 or 1, where (i+j+k) is 0 or 1. n denotes 0, 1 or 2.

12 Claims, No Drawings

SILACYCLOHEXANE COMPOUND, A METHOD OF PREPARING IT AND A LIQUID CRYSTAL COMPOSITION CONTAINING IT

BACKGROUND OF THE INVENTION

1. Field of the Invention

This invention relates to a new silacyclohexane compound, a method of preparing it, and a liquid crystal composition which contains it, as well as a liquid crystal display element containing said liquid crystal composition.

2. The Prior Art

A liquid crystal display element utilizes the optical anisotropy and dielectric anisotropy of liquid crystal substances. Display methods include the TN mode (twisted nematic mode), the STN mode (super twisted nematic mode), the SBE mode (super birefringence mode), the DS mode (dynamic scattering mode), the guest-host mode, the DAP mode ("deformation of aligned phase" mode) and the OMI mode (optical mode interference mode). The most common display device has a twisted nematic structure based on the Schadt-Helfrich mode.

The properties required of the liquid crystal substance used in these liquid crystal displays are somewhat different depending on the display method. However, a wide liquid crystal temperature range and stability with regard to moisture, air, light, heat, electric fields, etc., are properties commonly required by all display methods. Furthermore, it is desirable for the liquid crystal material to have a low viscosity, and also to have a short address time, low threshold voltage and high contrast in the cell(s).

Currently, there is no single compound which satisfies all these requirements. In practice, liquid crystal mixtures are used which are obtained by mixing several to more than ten liquid crystal compounds and latent liquid crystal compounds. Because of this, it is also important that the components of a liquid crystal composition mix easily.

Of these components, the following compound has been known as a compound which has both a high $T_{NI}$ (nematic-isotropic transition temperature) and a high $\Delta n$ (anisotropy of the refractive index).

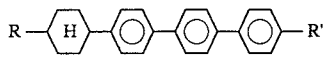

(See Japanese unexamined patent publication Tokkai Sho 58-203922.)

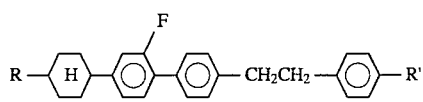

(See Japanese unexamined patent publication Tokuhyo Hei 3-503651.)

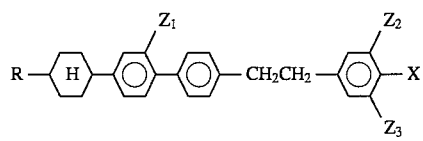

($Z_1$, $Z_2$ and $Z_3$ each independently denote H or F, and X denotes F, CN or Cl.) (See Tokuhyo Hei 3-503771.)

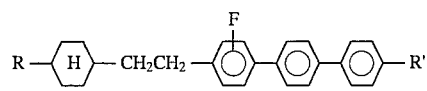

(See Japanese examined patent publication Tokko Hei 2-25894.)

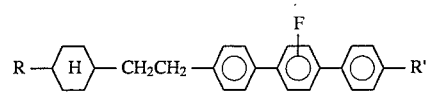

(See Tokko Hei 2-25894.)

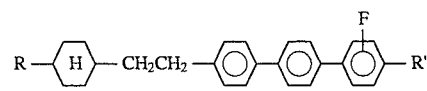

(See Tokko Hei 2-25894.)

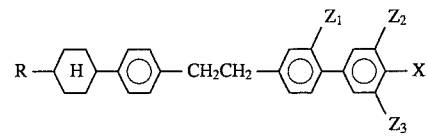

($Z_1$, $Z_2$ and $Z_3$ each independently denote H or F, and X denotes F, CN or Cl) (See Tokuhyo Hei 3-503771.)

In recent years, along with the expansion of the applications of liquid crystal displays. the characteristics required of liquid crystal materials are becoming more and more advanced. Also, driving methods and operation modes are becoming progressively more diversified.

For automobile onboard use in particular, because of the environment in which they are used, liquid crystal materials with their nematic phase extended to a high temperature range are required. The nematic phase can be extended to a high temperature by adding a liquid crystal compound(s) with a high $T_{NI}$ (nematic-isotropic transition temperature) as a component.

While the STN mode (super twisted nematic mode) is one of the operational modes which has been known. recent development of the active addressing drive method improved its shortcoming, i.e. slow response time, and this method is being put into practical use. For the liquid crystal material to be used in this method, a liquid crystal material with a high $\Delta n$ (anisotropy of the refractive index) is required because the cell gap is made narrower.

On the other hand, the PDLC (polymer dispersion liquid crystal) mode or PNLC (polymer network liquid crystal) mode has been proposed as a new display method and the development is under way toward practical use. Since all of these modes are scattering modes, a liquid crystal material with a large $\Delta n$ is required to increase the contrast.

BRIEF SUMMARY OF THE INVENTION

The object of this invention is to provide a conventionally unknown and completely new liquid crystal compound containing silacyclohexane rings with a silicon atom(s) in its molecular structure which has both a high $T_{NI}$ and a large $\Delta n$.

This invention provides a silacyclohexane compound represented by the following general formula (I).

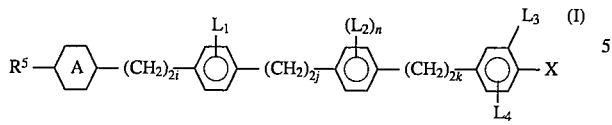

where R denotes a linear-chain alkyl group with a carbon number of 1–10, a fluoroalkyl group with a carbon number of 1–10 in which a fluorine atom(s) is substituted for one or two hydrogen atoms, a branched-chain alkyl group with a carbon number of 3–8, an alkoxyalkyl group with a carbon number of 2–7, or an alkenyl group with a carbon number of 2–8. n denotes 0, 1 or 2.

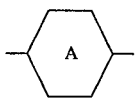

denotes a trans-1-sila-1,4-cyclohexylene or trans-4-sila-1,4-cyclohexylene group whose silicon at position 1 or position 4 has a substitutional group(s) of H, F, Cl or $CH_3$. $L_1$ and $L_2$ independently denote H or F. $L_3$ and $L_4$ independently denote H, F or Cl. X denotes a H, CN, F, Cl, $CF_3$, $CF_2Cl$, $CHFCl$, $OCF_3$, $OCF_2Cl$, $OCHFCl$, $OCHF_2$, or a linear-chain alkyl or alkoxy group with a carbon number of 1–10. i, j and k denote 0 or 1, where (i+j+k) is 0 or 1.

This invention also provides a silacyclohexane compound represented by the following general formula (II).

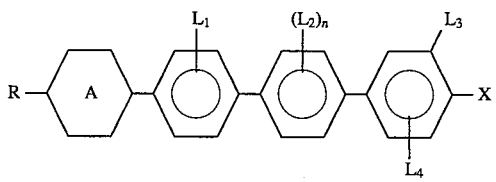

Where, R,

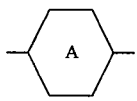

$L_1$, $L_2$, $L_3$, $L_4$, X and n are the same as those in the general formula (I).

This invention also provides a silacyclohexane compound represented by the following general formula (III).

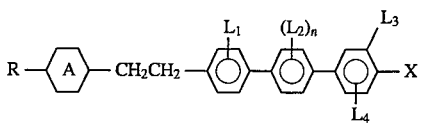

Where, R,

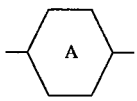

$L_1$, $L_2$, $L_3$, $L_4$, X and n are the same as those in the general formula (I).

This invention also provides a silacyclohexane compound represented by the following general formula (IV).

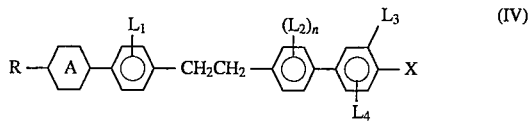

Where, R,

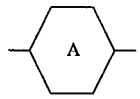

$L_1$, $L_2$, $L_3$, $L_4$, X and n are the same as those in the general formula (I).

This invention also provides a silacyclohexane compound represented by the following general formula (V).

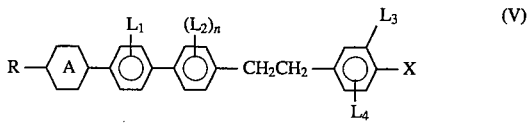

Where, R,

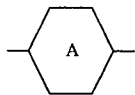

$L_1$, $L_2$, $L_3$, $L_4$, X and n are the same as those in the general formula (I).

This invention also provides a method of preparing the silacyclohexane compound represented by said general formula (I) characterized by the use of a reaction selected from a carbon-silicon bond formation reaction and a carbon-carbon bond formation reaction including a de-MQ reaction between an organometallic reagent

R—M (in this formula, M denotes MgP (P denotes a halogen), ZnP or Li) and a silacyclohexane compound

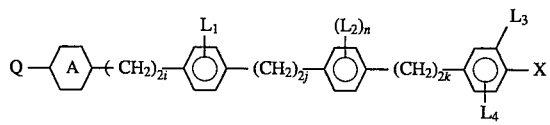

(Q denotes a halogen atom, or an alkoxy, methansulfonyloxy, benzenesulfonyloxy, p-toluenesulfonyloxy or perfluoroalkanesulfonyloxy group).

This invention also provides a method of preparing the silacyclohexane compound represented by said general formula (I) characterized by the use of a carbon-carbon bond formation reaction including a de-M'Q reaction between an organometallic reagent

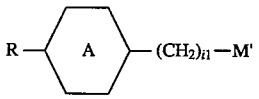

(M' denotes M or $B(OY)_2$ (Y denotes H or an alkyl group) and a compound

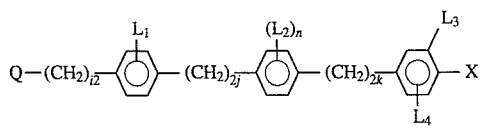

In this formula, i1 and i2 respectively denote 0, 1 or 2, where (i1+i2) is 0 or 2. Also, j and k respectively denote 0 or 1, where {(i1+i2)+2j+2K} is 0 or 2.

This invention also provides a method of preparing the silacyclohexane compound represented by said general formula (I) characterized by the use of a carbon-carbon bond formation reaction including a de-MQ' reaction between an organometallic reagent

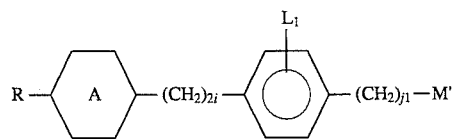

and a compound

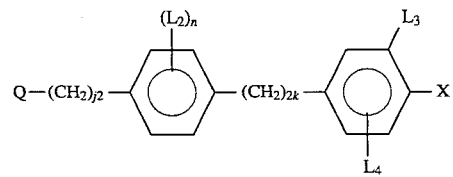

In this formula, j1 and j2 respectively denote 0, 1 or 2 where (j1+j2) is 0 or 2. Also, i and k respectively denote 0 or 1 where {2i+(j1+j2)+2k} is 0 or 2.

This invention also provides a method of preparing the silacyclohexane compound represented by said general formula (I) characterized by the use of a carbon-carbon bond formation reaction including a de-M'Q reaction between a silacyclohexane compound

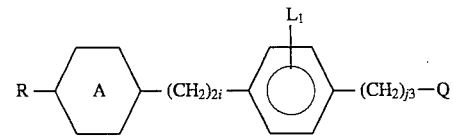

and an organometallic reagent

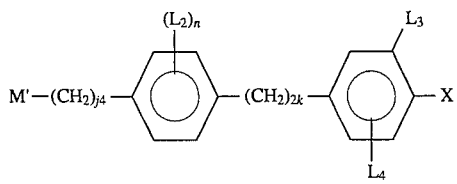

In this formula, j3 and j4 respectively denote 0, 1 or 2 where (j3+j4) is 0 or 2, Also, i and k respectively denote 0 or 1 where {2i+(j3+j4)+2k} is 0 or 2.

This invention also provides a method of preparing the silacyclohexane compound represented by said general formula (I) characterized by the use of a carbon-carbon bond formation reaction including a de-M'Q reaction between a silacyclohexane compound

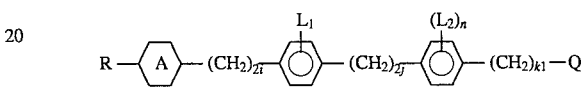

and an organometallic reagent

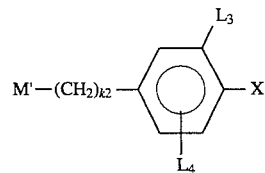

In this formula, k1 and k2 respectively denote 0, 1 or 2 where (k1+k2) is 0 or 2. Also, i and j respectively denote 0 or 1 where {2i+2j+(k1+k2)} is 0 or 2.

Furthermore, this invention provides a liquid crystal composition characterized by containing the silacyclohexane compound represented by said general formula (I) and a liquid crystal display element characterized by containing this liquid crystal composition.

Specific examples of the silacyclohexane compound represented by said general formula (I) are shown below and a detailed description follows.

Examples of the silacyclohexane compound of this invention are those represented by ring structures containing a trans-1- or trans-4-silacyclohexane ring shown below.

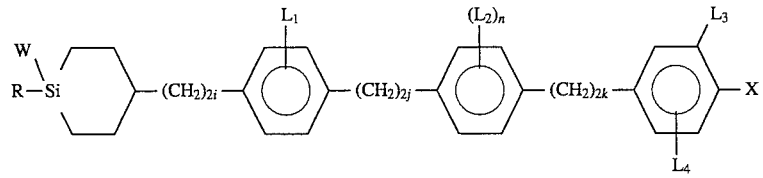

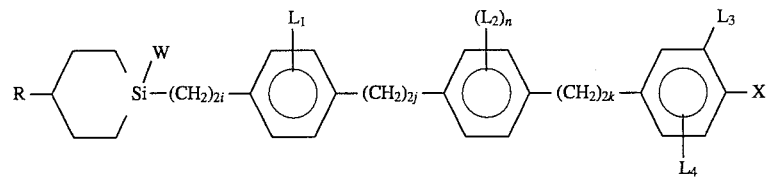

Specific examples follow.

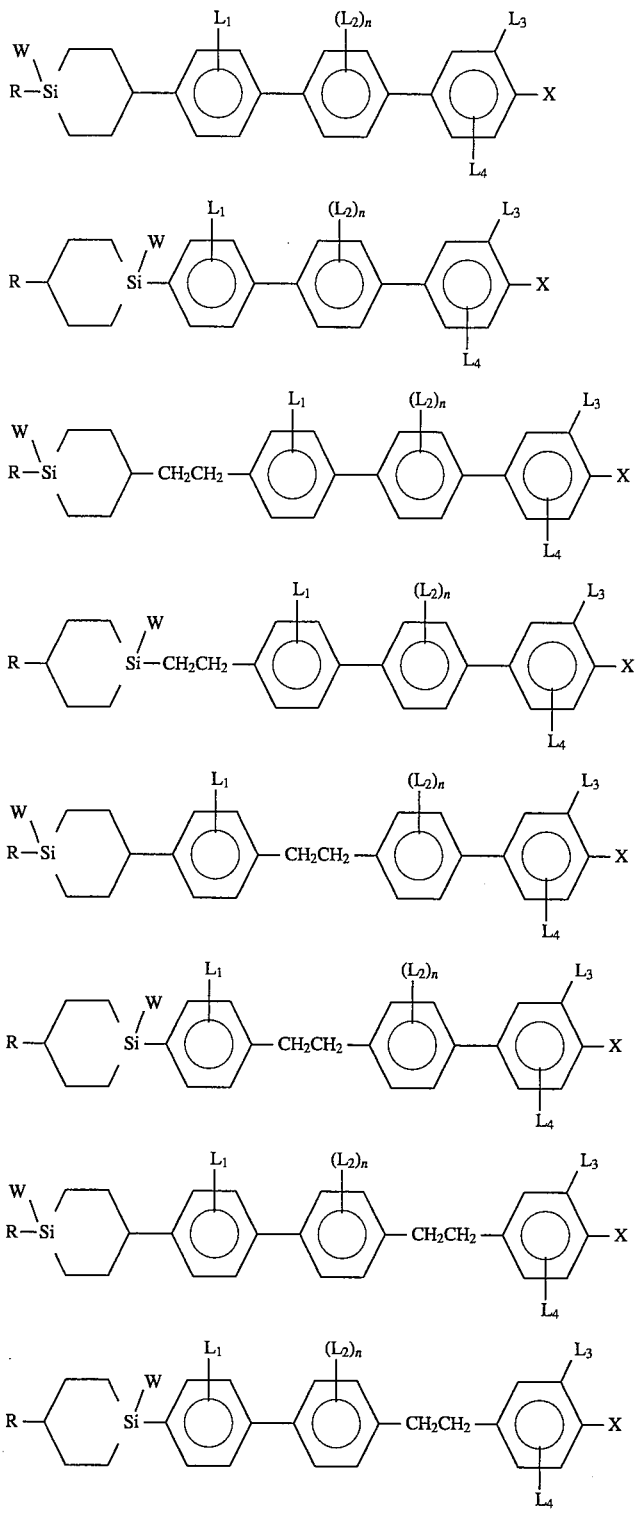

R denotes one of the following:
(a) A linear-chain alkyl group with a carbon number of 1–10, i.e. a methyl, ethyl, n-propyl, n-butyl, n-pentyl, n-hexyl, n-heptyl, n-octyl, n-nonyl or n-decyl group (b) A mono- or di-fluoroalkyl group with a carbon number of 1–10, i.e. fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluoobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl or 10,10-difluorodecyl group (c) A branched-chain alkyl group with a carbon number of 3–8, i.e. an isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl or 3-methylheptyl group (d) An alkoxyalkyl group with a carbon number of 2–7, i.e. a methoxymethyl, ethoxymethyl, propoxymethyl, butoxymethyl, pentoxymethyl, hexyloxymethyl, methoxyethyl, ethoxyethyl, propoxyethyl, butoxyethyl, methoxypropyl, ethoxypropyl, propoxypropyl, butoxypropyl, methoxybutyl, ethoxybutyl, propoxybutyl, methoxypentyl, ethoxypentyl or methoxyhexyl group (e) An alkenyl group with a carbon number of 2–8, i.e. a vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl or 7-octenyl group denotes H, F, Cl or $CH_3$.

$L_1$ and $L_2$ independently denote H or F. $L_3$ and $L_4$ independently denote H, F or Cl. X denotes H, CN, F, Cl, $CF_3$, $CF_2Cl$, $CHFCl$, $OCF_3$, $OCF_2Cl$, $OCHFCl$, $OCHF_2$ or one of the following:

(f) A linear-chain alkyl group with a carbon number of 1–10, i.e. a methyl, ethyl, n-propyl, n-butyl, n-pentyl, n-hexyl, n-heptyl, n-octyl, n-nonyl or n-decyl group (g) A linear-chain alkoxy group with a carbon number of 1–10, i.e. a methoxy, ethoxy, n-propoxy, n-butoxy, n-pentoxy, n-hexyloxy, n-heptyloxy, n-octyloxy, n-nonyloxy or n-decyloxy group Specific examples of the partial structures

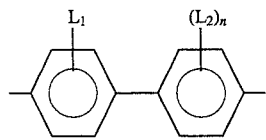

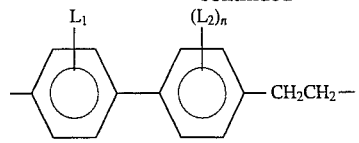

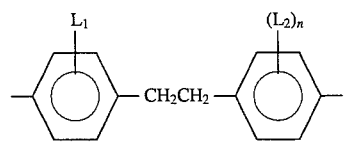

and

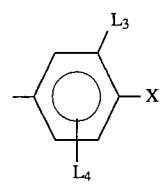

in the silacyclohexane compound represented by said general formula (I) follow.

Examples of the partial structure

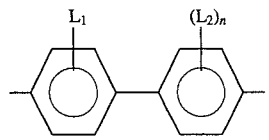

are listed below.

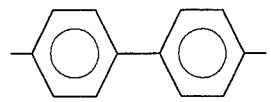

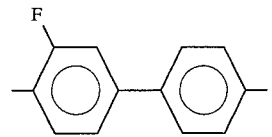

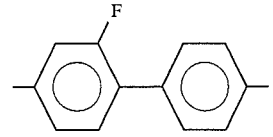

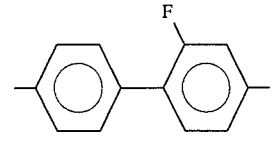

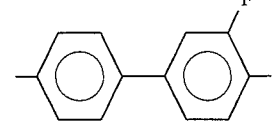

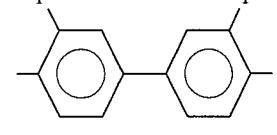

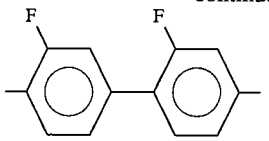
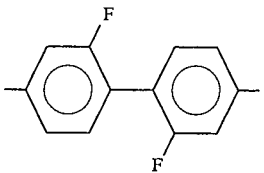
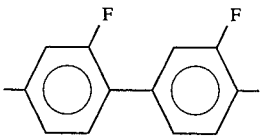
Examples of the partial structure
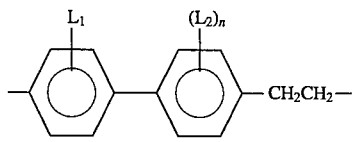
are listed below.
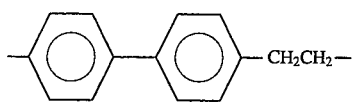
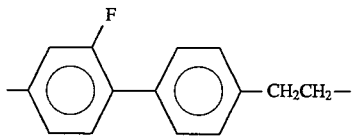
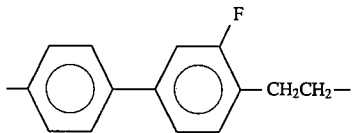
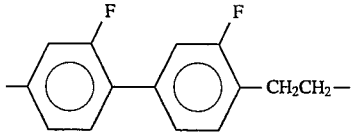
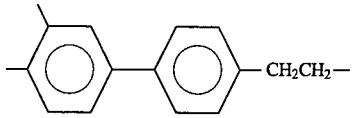
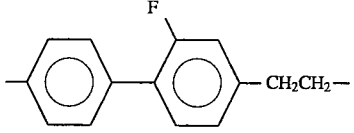
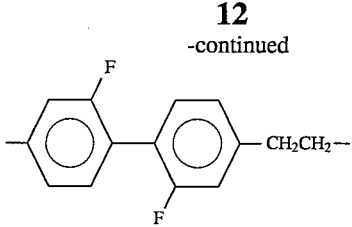
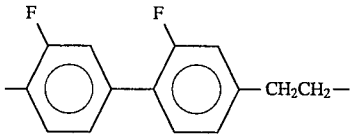
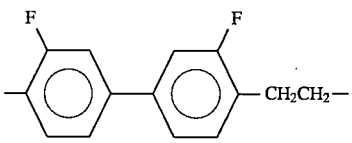
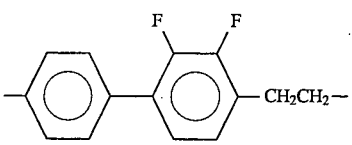
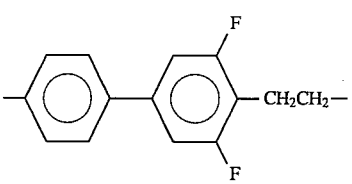
Examples of the partial structure
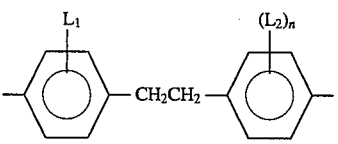
are listed below.
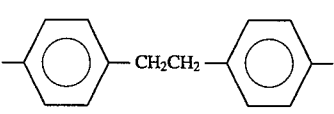
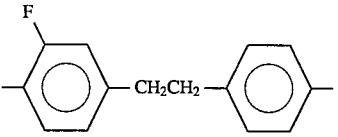
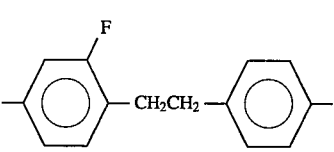
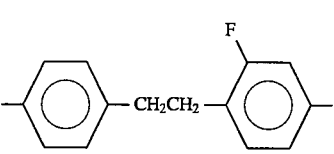

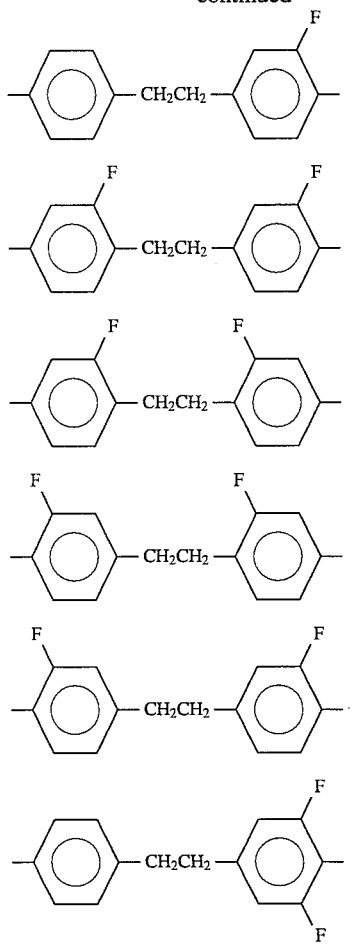
Examples of the partial structure
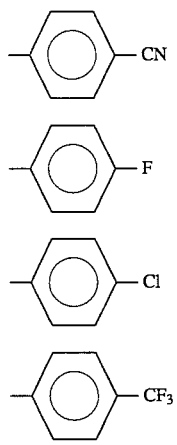
are listed below.
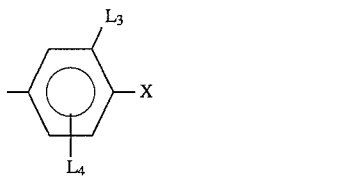
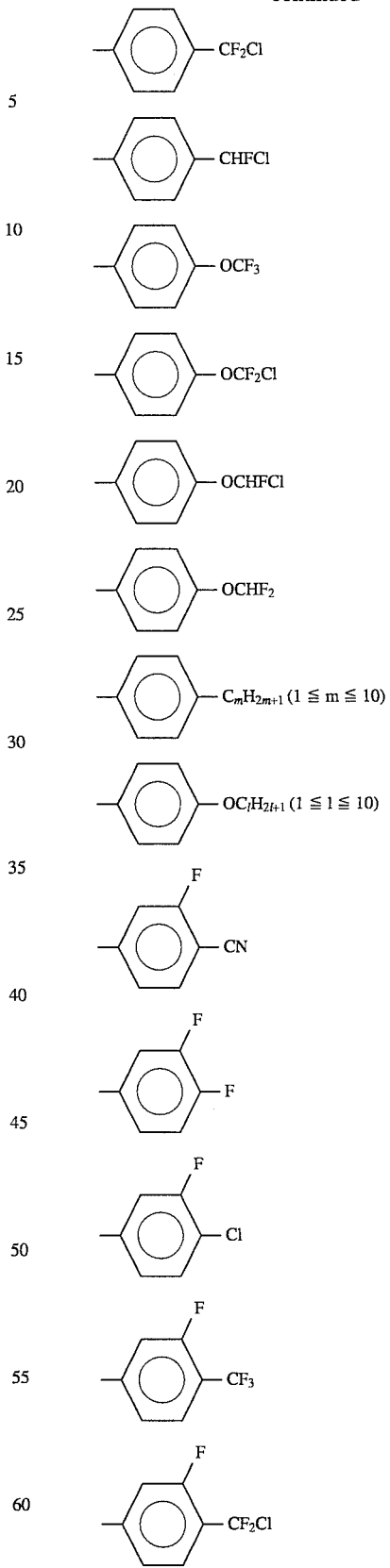

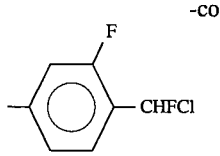
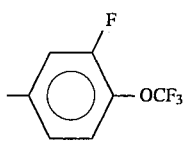
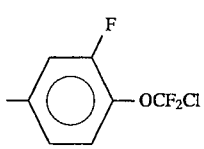
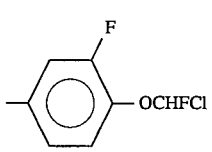
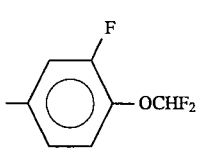
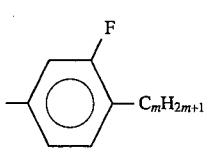
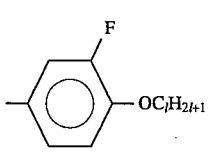
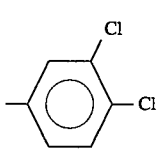
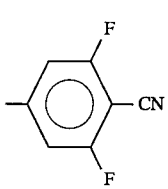
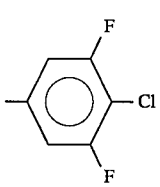
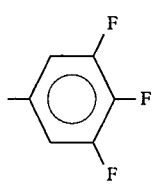
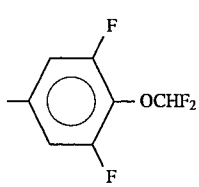
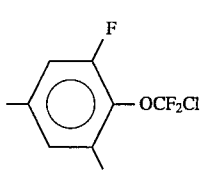
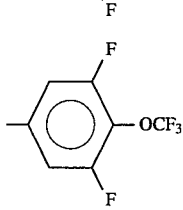
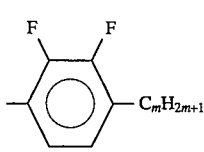
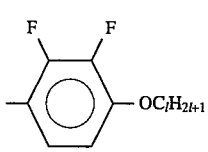
Of these, the following are particularly preferable because of their wider liquid crystal temperature region.
For the ring structure, the structure represented by

[Structure diagram:]

W\
R—Si—(CH₂)₂ᵢ—[ring with L₁]—(CH₂)₂ⱼ—[ring with (L₂)ₙ]—(CH₂)₂ₖ—[ring with L₃, L₄]—X is preferable.

For R, one of the following is preferable:

(h) A linear-chain alkyl group with a carbon number of 2–7, i.e. an ethyl, n-propyl, n-butyl, n-pentyl, n-hexyl or n-heptyl group, or some branched-chain alkyl groups including isopropyl, 1-methylpropyl, 2-methylpropyl, 1-methylbutyl, 2-methylbutyl, 3-methylbutyl, 1-methylpentyl, 2-methylpentyl and 2-ethylhexyl groups (i) Some mono- or di-fluoroalkyl groups with a carbon number of 1–10 including 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 6-fluorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 6,6-difluorohexyl, 6,6-difluoroheptyl and 7,7-difluoroheptyl groups (j) An alkoxyalkyl group with a carbon number of 2–6, i.e. a methoxymethyl, methoxyethyl, methoxypropyl, methoxypentyl, ethoxymethyl, ethoxyethyl, propoxymethyl or pentoxymethyl group (k) Some alkenyl groups including vinyl, 1-propenyl, 3-butenyl, 1-pentenyl, 3-pentenyl, 4-pentenyl, 1-hexenyl, 5-hexenyl, 6-heptenyl and 7-octenyl groups H, F and a CH₃ group are preferable for W.

For

[biphenyl with L₁ and (L₂)ₙ substituents]

the following are preferable.

[biphenyl]

[biphenyl with F]

[biphenyl with F]

[biphenyl with two F]

[biphenyl with two F]

in practical use.

For

[biphenyl-CH₂CH₂— with L₁ and (L₂)ₙ]

following are preferable in practical use.

[biphenyl-CH₂CH₂—]

[biphenyl-CH₂CH₂— with F]

[biphenyl-CH₂CH₂— with F]

[biphenyl-CH₂CH₂— with two F]

[biphenyl-CH₂CH₂— with two F]

For the partial structure
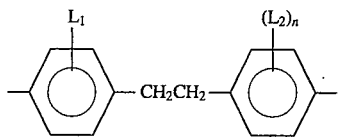
the following are preferable.
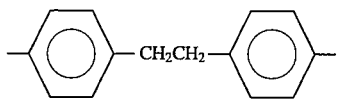
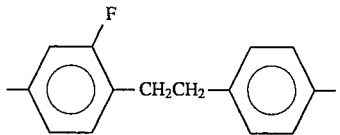
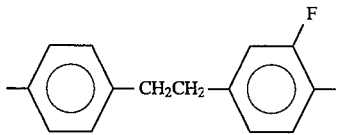
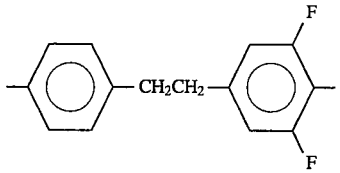
For the partial structure
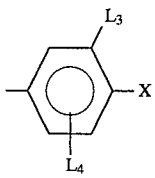
the following are preferable.
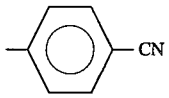
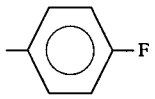
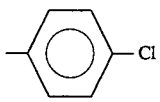
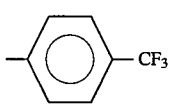
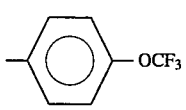
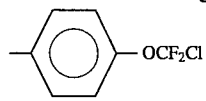 —OCF$_2$Cl
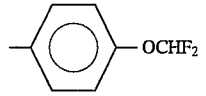 —OCHF$_2$
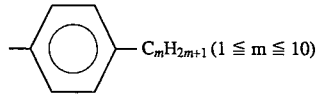 —C$_m$H$_{2m+1}$ (1 ≦ m ≦ 10)
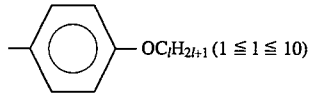 —OC$_l$H$_{2l+1}$ (1 ≦ l ≦ 10)
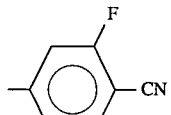 —CN
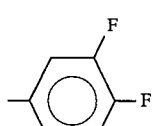 —F
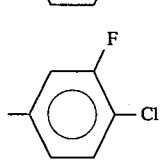 —Cl
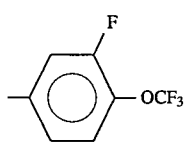 —OCF$_3$
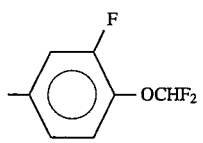 —OCHF$_2$
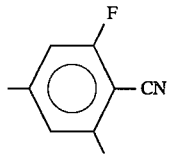 —CN
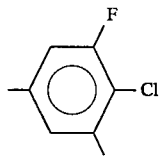 —Cl -continued

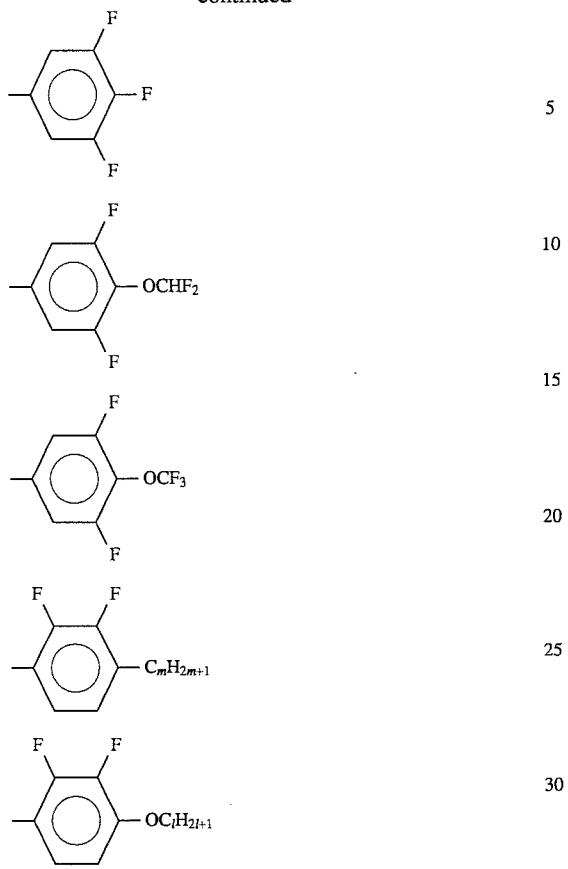

in practical use.

These compounds are prepared by a carbon-silicon bond formation reaction or carbon-carbon bond formation reaction between an organometallic reagent and a compound which has an eliminatable group(s) such as a halogen atom, an alkoxy group or a perfluoroalkanesulfonyloxy group. A detailed description of a method of manufacturing these compounds is given below.

In the carbon-silicon bond formation reaction including the de-MQ reaction between the organometallic reagent

R—M (in this formula, M denotes MgP (P denotes a halogen atom), ZnP or Li) and the silacyclohexane compound

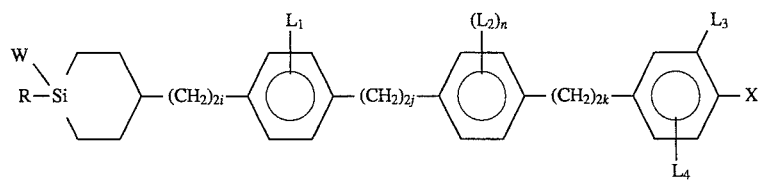

(W denotes H, F, Cl or a $CH_3$ group, and Q denotes a halogen atom or an alkoxy group), or in the carbon-silicon bond formation reaction including the de-MQ reaction between the organometallic reagent

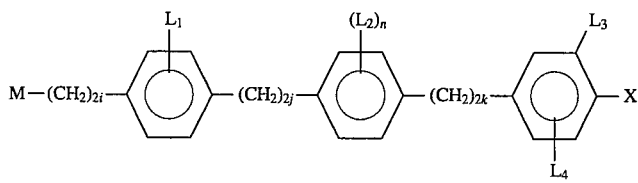

and the silacyclohexane compound

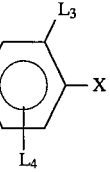

the reaction normally requires no catalyst, but a monovalent copper compound such as copper (I) chloride, copper (I) bromide, copper (I) iodide or copper (I) cyanide can be added as a catalyst.

Examples of Q are such as a halogen atom or an alkoxy group. It is particularly preferable if Q is a F, Cl or Br atom, or an $OCH_3$ or $OCH_2CH_3$ group, because then the target product can be obtained with a high yield.

In the carbon-carbon bond formation reaction including the de-M'Q' reaction between the organometallic reagent

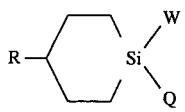

(in this formula, M' denotes MgP (P denotes a halogen atom), ZnP, Li or $B(OY)_2$ (Y denotes H or an alkyl group)) and

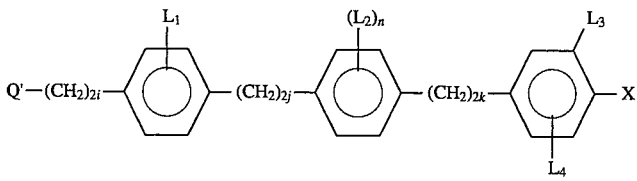

(in this formula, Q' denotes a halogen atom or a perfluoroalkanesulfonyloxy group), or the carbon-carbon bond formation reaction including the de-M'Q' reaction between the organometallic reagent

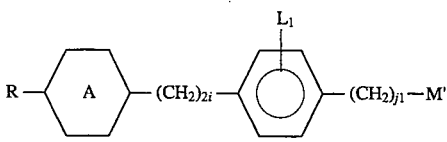

and

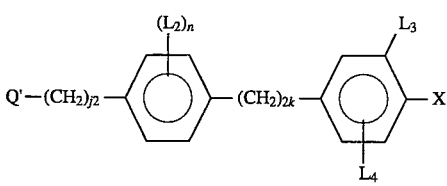

or the carbon-carbon bond formation reaction including the de-M'Q' reaction between the organometallic reagent

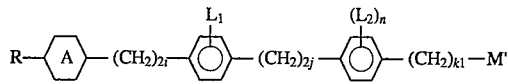

and

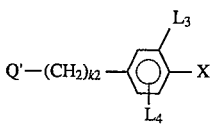

or the carbon-carbon bond formation reaction including the de-M'Q' reaction between the organometallic reagent

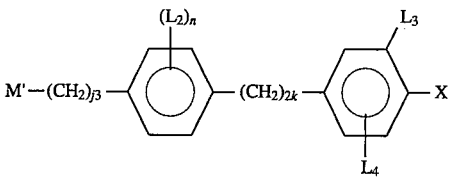

and

-continued

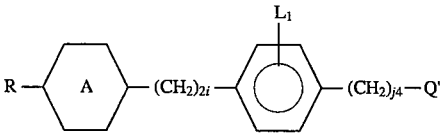

or the carbon-carbon bond formation reaction including the de-M'Q' reaction between the organometallic reagent

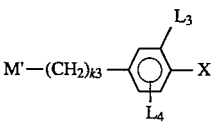

and

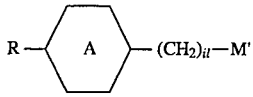

when all i2, j2, k2, j4 and k4 are 0, the reaction is carried out in the presence of a transition metal catalyst. A palladium or nickel compound is particularly preferable for the catalyst, giving the object compound with a high yield.

Examples of the palladium catalysts are zero-valent palladium compounds such as tetrakis (triphenylphosphine) palladium (0) and di[1,2-bis(diphenylphosphino)ethane]palladium (0), and compounds composed of a divalent palladium compound such as palladium acetate and palladium chloride and a ligand(s), as well as a combination of these and a reducing agent.

Examples of the nickel catalysts are divalent nickel compounds such as 1,3-bis(diphenylphosphino)propane nickel (II) chloride, 1,2-bis(diphenylphosphino)ethane nickel (II) chloride and bis(triphenylphosphine) nickel (II) chloride, and zero-valent nickel compounds such as tetrakis (triphenylphosphine) nickel (0).

When the eliminatable group Q' is a perfluoroalkanesulfonyloxy group, addition of a lithium salt such as lithium chloride and lithium bromide will improve the yield.

When the organometallic reagent is a boric acid derivative, i.e. when M' is B $(OY)_2$, the reaction should preferably be carried out in the presence of a base. For the base, for example, inorganic bases such as sodium carbonate, sodium bicarbonate, potassium carbonate, sodium hydroxide and potassium hydroxide, and organic bases such as triethylamine, tributylamine and dimethylaniline can be used. In this case, a halogen atom is preferable for Q.

When all i2, j2, k2, j4 and k4 are 1 or 2, the carbon-carbon bond formation reaction is carried out in the presence of a catalytic amount of copper salt. Examples of the copper salt are mono-copper salt such as copper (I) chloride, copper (I) bromide, copper (I) iodide or copper (I) cyanide, di-copper salt such as copper (II) chloride, copper (II) bromide, copper (II) iodide or copper (II) acetate, copper complex such as di-lithium tetrachlorocuprate, etc. Br or I are preferable for Q, giving the target compound with a high yield.

Following a conventional after treatment, the product obtained by the reactions described above is purified to obtain the silacyclohexane compound of this invention. If the obtained silasiclyhexane compound is a mixture of trans isomers and cis isomers in terms of the conformation of the silacyclohexane ring, a conventional purification means such as chromatography and recrystallization is employed to separate the trans isomers.

A compound used for mixing with the silacyclohexane compound of this invention to obtain the liquid crystal phase can be chosen from among the known compounds shown below:

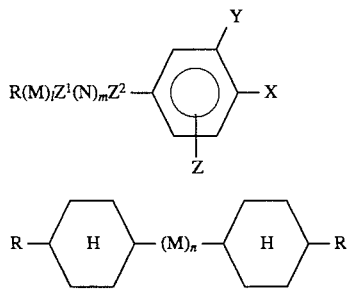

In the above formulas, (M) and (N) denote one of the following items 1) through 5):
1) A trans-1,4-cyclohexylene group which has no substitution or which has one or more substitutional groups such as F, Cl, Br, CN or alkyl groups
2) A trans-1,4-cyclohexylene group which has O or S substituted for one or nonadjacent two $CH_2$ groups in the cyclohexane ring
3) A 1,4-cyclohexenylene group
4) A 1,4-phenylene group which has no substitution or which has one or two substitutional groups such as F, Cl, $CH_3$ or CN groups
5) A 1,4-phenylene group which has an N atom substituted for one or two CH groups.

$Z_1$ and $Z_2$ each denote —$CH_2CH_2$—, —CH=CH—, —C≡C—, —$CO_2$—, —OCO—, —$CH_2O$—, —$OCH_2$— or a single bond.

l, m=0, 1 or 2 (where l+m=1, 2 or 3), and n=0, 1 or 2.

R denotes a linear-chain alkyl group with a carbon number of 1–10, an alkoxy group, a branched-chain alkyl group with a carbon number of 3–8, an alkoxyalkyl group with a carbon number of 2–7, or an alkenyl group with a carbon number of 2–8.

X denotes a H, CN, F, Cl, $CF_3$, $CF_2Cl$, CHFCl, $OCF_3$, $OCF_2$ Cl, OCHFCl, $OCHF_2$, or a linear-chain alkyl or alkoxy group with a carbon number of 1–10.

Y and Z independently denote H, F, Cl or $CH_3$.

If l=2 and n=2, then (M) can contain heterogeneous rings, and if m=2, then (N) can contain heterogeneous rings.

The ratio of one or more types of the silacyclohexane compound of this invention contained in the liquid crystal composition is 1–50 wt %, more preferably 5–30 wt %. The liquid crystal composition can also contain a polygenetic dye(s) to generate a colored guest-host system and additives to change the dielectric anisotropy, viscosity and the orientation of the nematic phase.

The liquid crystal phase thus formed is sealed between transparent base plates which have electrodes of desired shapes and is thus used as liquid crystal display elements. This element can have various undercoatings, overcoatings for orientation control, a polarizer plate(s), a filter(s) and a reflector layer(s), as necessary. It can be made into a laminated cell or combined with other display elements. Semiconductor substrates and light sources can also be used to make various types of displays.

For the driving method of the liquid crystal display element, prior-art methods in the industry of liquid crystal display elements, such as the dynamic scattering (DSM) method, the twisted nematic (TN) method, the super twisted nematic (STN) method, the guest-host (GH) method, the polymer dispersion (PDLC) method and the polymer network (PNLC) method can be adopted.

EXAMPLE

The details of this invention are described below by referring to specific examples.

Example 1

Preparation of 4-(trans-4-n-pentyl-4-silacyclohexyl)-4"-fluoroterphenyl

A 6 ml tetrahydrofuran solution of 2.0M n-pentyl magnesium chloride was dripped into a mixture of 8.81 g of 4-(4-chloro-4-silacyclohexyl)-4"-fluoroterphenyl and 20 ml of tetrahydrofuran. After a conventional after treatment, the product was purified by means of chromatography to obtain 4.01 g (yield 96%) of the trans isomer, which is the target product.

$C$-$S_1$ transition temperature: 179° C.,
$S_1$-$S_2$ transition temperature: 225° C.,
$S_2$-N transition temperature: 234° C.,
N-I transition temperature: 256° C.

IR (KBr disc) νmax: 2916, 2852, 2098, 1493, 1240, 1161 and 811 cm$^{-1}$

The following compounds shown in Examples 2–6 were obtained in the same manner as Example 1.

Example 2

4-(trans-4-n-pentyl-4-silacyclohexyl)-3"-fluoro-4"-trifluoromethoxyterphenyl

Example 3

4-(trans-4-n-pentyl-4-silacyclohexyl)-4"-cyano-3",5"-difluoroterphenyl

Example 4

4-(trans-4-n-pentyl-4-silacyclohexyl)-2",3"-difluoro-4"-n-propylterphenyl

Example 5

4-(trans-4-(4-methylpentyl)-4-silacyclohexyl)-4"-trifluoromethylterphenyl

Example 6

4-(trans-4-(4-methylpentyl)-4-silacyclohexyl)-3",4"-difluoroterphenyl

Example 7

Preparation of 4-(trans-4-n-propyl-1-silacyclohexyl)-2,4"-difluoroterphenyl

A 20 ml tetrahydrofuran solution of 0.8M 3-fluoro-4-(4-(p-fluorophenyl)phenyl)phenyl magnesium bromide was dripped into a mixture of 1.77 g of 1-chloro-4-n-propyl-1-silacyclohexane, 15 ml of isooctane and 20 mg of copper (I) cyanide. After a conventional after treatment, the product was purified by means of chromatography to obtain 3.21 g (yield 79%) of the trans isomer, which is the target product.

Example 8

Preparation of 4-(trans-4-n-pentyl-4-silacyclohexyl)-2,4"-difluoroterphenyl

A 10 ml tetrahydrofuran solution of 1.0M 2-fluoro-4-(trans-4-n-pentyl-4-silacyclohexyl)phenyl magnesium bromide was dripped into a mixture of 2.51 g of 4-bromo-4'-fluorobiphenyl, 50 mg of bis(1,3-diphenylphosphinopropane) nickel (II) chloride and 30 ml of tetrahydrofuran. After a conventional after treatment, the product was purified by means of chromatography to obtain 3.85 g (yield 89%) of the target product.

C-S transition temperature: 88° C.,
S-N transition temperature: 135° C.,
N-I transition temperature: 250° C.
IR (KBr disc) νmax: 2918, 2846, 2106, 1487, 1223, 887 and 816 cm$^{-1}$ The following compounds shown in Examples 9–11 were obtained in the same manner as Example 8.

Example 9

4-(trans-4-n-pentyl-4-silacyclohexyl)-2-fluoro-4"-chloroterphenyl

Example 10

4-(trans-4-n-pentyl-4-silacyclohexyl)-2-fluoro-4"-trifluoromethoxyterphenyl

Example 11

4-(trans-4-n-pentyl-4-silacyclohexyl)-2,3",4",5"-tetrafluoroterphenyl

Example 12

Preparation of 4-(trans-4-n-butyl-1-methyl-1-silacyclohexyl)-4"-cyanoterphenyl

A 20 ml tetrahydrofuran solution of 0.5M trans-4-(4-(1-methyl-4-n-butyl-4-silacyclohexyl)phenyl)phenyl zinc chloride was dripped into a mixture of 3.50 g of p-iodobenzonitrile, 70 mg of tetrakis (triphenylphosphine) palladium (0) and 20 ml of tetrahydrofuran. After a conventional after treatment, the product was purified by means of chromatography to obtain 3.33 g (yield 79%) of the target product.

C-S transition temperature: 117° C.,
S-N transition temperature: 175° C.,
N-I transition temperature: 192° C
IR (KBr disc) νmax: 2922, 2845, 1487, 1402, 1250, 837 and 810 cm$^{-1}$ The following compounds shown in Examples 13–16 were obtained in the same manner as Example 12.

Example 13

4-(trans-4-n-pentyl4-silacyclohexyl)-2-fluoro-4"-n-propylterphenyl

Example 14

4-(trans-4-(3-methoxypropyl)-4-silacyclohexyl)-2,3",4"-trifluoroterphenyl

Example 15

4-(trans-4-n-propyl-4-silacyclohexyl)-3-fluoro-4"-cyanoterphenyl

Example 16

4-(trans-4-n-propyl-4-silacyclohexyl)-3,3"-difluoro-4"-chloroterphenyl

Example 17

Preparation of 4-(trans-4-n-pentyl-4-silacyclohexyl)-3",4"-difluoroterphenyl

A 30 ml. tetrahydrofuran solution of 0.5M 4-(3,4-difluorophenyl)phenyl zinc chloride was dripped into a mixture of 3.95 g of 4-(trans-4-n-pentyl-1-silacyclohexyl) phenyltrifluoromethanesulfonate, 50 mg of tetrakis (triphenylphosphine) palladium (0), 1.50 g of lithium chloride and 50 ml of N,N-dimethylformamide. After a conventional after treatment, the product was purified by means of chromatography to obtain 4.20 g (yield 97%) of the target product.

C-S transition temperature: 120° C.,
S-N transition temperature: 195° C.,
N-I transition temperature: 240° C.
IR (KBr disc) νmax: 2916, 2854, 2110, 1495, 985, 887 and 810 cm$^{-1}$ The following compounds shown in Examples 18–20 were obtained in the same manner as Example 17.

Example 18

4-(trans-4-n-propyl-4-silacyclohexyl)-3-fluoro-4''-n-pentyloxyterphenyl

Example 19

4-(trans-4-n-propyl-4-silacyclohexyl)-3,2'',3''-trifluoro-4-n-pentyloxyterphenyl

Example 20

4-(trans-4-(3-pentenyl)-4-silacyclohexyl)-3–,4''-difluoroterphenyl

Example 21

Preparation of 4-(trans-4-n-pentyl-4-silacyclohexyl)-2,3'',4''-trifluoroterphenyl A 4.48 g of 4-(trans-4-n-pentyl-4-silacyclohexyl)-4''-iodobiphenyl, dissolved in 20 ml of benzene, was dripped into a mixture of 2.00 g of 3,4-difluorophenylboric acid, 35 mg of tetrakis (triphenylphosphine) palladium (0) and a 20 ml aqueous solution of 2M sodium carbonate. After a conventional after treatment, the product was purified by means of chromatography to obtain 3.98 g (yield 88%) of the target product.

C-S transition temperature: 66° C.,
S-N transition temperature: 93° C.,
N-I transition temperature: 166° C.
IR (KBr, disc): 2912, 2848, 2096, 1491, 1396, 1313, 1180, 989, 873 and 812 cm$^{-1}$ The following compounds shown in Examples 22–28 were obtained in the same manner as Example 21.

Example 22

4-(trans-4-n-propyl-4-silacyclohexyl)-2',3''-difluoro-4''-cyanoterphenyl

Example 23

4-(trans-4-n-propyl-4-silacyclohexyl)-2',3'', 5''-trifluoro-4''-difluoromethoxyterphenyl

Example 24

4-(trans-4-methyl-n-pentyl-4-silacyclohexyl)-2'-fluoro-4''-chloroterphenyl

Example 25

4-(trans-4-n-pentyl-4-silacyclohexyl)-3',4''-difluoroterphenyl

Example 26

4-(trans-4-n-pentyl-4-silacyclohexyl)-3'-fluoro-4''-trifluoromethoxyterphenyl

Example 27

4-(trans-4-n-propyl-4-silacyclohexyl)-3',4''-difluoroterphenyl

Example 28

4-(trans-4-n-propyl-4-fluoro-4-silacyclohexyl)-4''-chloroterphenyl

Example 29

A mixture A comprising 45 mole % of trans-4-(2-(trans-4-(3,4-difluorophenyl)cyclohexyl)ethyl)-1-n-ethyl-1-cyclohexane, 15 mole % of trans-4-(2-(trans-4-(3,4-difluorophenyl)cyclohexyl)ethyl)-1-n-propyl-1-cyclohexane and 40 mole % of trans-4-(2-(trans-4-(3,4-difluorophenyl)cyclohexyl)ethyl)-1-n-pentyl-1-cyclohexane exhibits the following characteristics: $T_{NI}$ (nematic-isotropic transition temperature)=96° C. $\Delta n$ (anisotropy of the refraction index at 25° C.)=0.0718

A mixture comprising 85 mole % of this mixture A and 15 mole % of the 4-(trans-4-n-pentyl-4-silacyclohexyl)-2,4''-difluoroterphenyl obtained in Example 8 exhibited an increase in both $T_{NI}$ and $\Delta n$, as shown below.

$T_{NI}$=119° C.
$\Delta n$=0.0955

Example 30

Preparation of trans-4-(4-n-pentyl-4-silacyclohexyl)-2-fluoro-4'-(2-(3,4-difluorophenyl)ethyl)biphenyl An 8 ml tetrahydrofuran solution of 2.0M n-pentyl magnesium chloride was dripped into a mixture of 4.45 g of 4-(4-chloro-4-silacyclohexyl)-2-fluoro-4'-(2-(3,4-difluorophenyl)ethyl)biphenyl and 30 ml of tetrahydrofuran, and the resulting mixture was stirred for 8 hours at room temperature. After a conventional after treatment, the reaction mixture was purified by means of silica-gel chromatography to obtain 4.01 g (yield 83%) of the target product, i.e. the trans isomer.

IR (KBr disc): vmax: 2920, 2102, 1518, 1491, 1404, 1290, 1286, 1120, 889 and 818 cm$^{-1}$ C-S transition temperature: 49.5° C.,
S-N transition temperature: 50.6° C.,
N-I transition temperature: 150.5° C.

The following compounds were obtained in the same manner as Example 30.

Example 31

Trans-4-(4-n-pentyl4-silacyclohexyl)-2-fluoro-4'-(2-(4-chlorophenyl)ethyl)biphenyl

Example 32

Trans-4-(4-n-pentyl-4-silacyclohexyl)-2-fluoro-4'-(2-(4-trifluoromethoxyphenyl) ethyl)biphenyl

Example 33

Trans-4-(4-n-pentyl-4-silacyclohexyl)-2-fluoro-4'-(4-n-propoxyphenyl)ethyl)biphenyl

Example 34

Trans-4-(4-n-pentyl-4-silacyclohexyl)-2-fluoro-4'-(2-(4-trifluoromethylphenyl)ethyl)biphenyl

Example 35

Preparation of
trans-4-(4-n-pentyl-4-silacyclohexyl)-2-fluoro-4'-(2-(4-fluorophenyl)ethyl)biphenyl An 10-ml tetrahydrofuran-toluene (1:1) solution of 1.0M trans-4-(4-n-pentyl-4-silacyclohexyl)-2-fluorophenyl zinc chloride was dripped into a mixture of 3.48 g of 4-(2(4-fluorophenyl)ethyl)phenyltrifluoromethanesulfonate, 1.00 g of lithium chloride, 30 mg of tetrakis (triphenylphosphine) palladium (0) and 25 ml of N,N-dimethylformamide, and the resulting mixture was stirred for 5 hours at 60° C. After a conventional after treatment, the reaction mixture was purified by means of silica-gel chromatography to obtain 4.26 g (yield 92%) of the target product.

IR (KBr disc): νmax: 2916, 2104, 1508, 1493, 1404, 1221, 987, 887 and 816 cm$^{-1}$ C-S transition temperature: 63.1° C., S-N transition temperature: 52.2° C., N-I transition temperature: 161.9° C.

The following compounds were obtained in the same manner as Example 35.

Example 36

Trans-4-(4-n-propyl-4-silacyclohexyl)-2-fluoro-4'-(2-(3,4-difluorophenyl)ethyl)biphenyl

Example 37

Trans-4-(4-n-propyl-4-silacyclohexyl)-2-fluoro-4'-(2-(2,3,4-trifluorophenyl)ethyl)biphenyl

Example 38

Trans-4-(4-n-propyl-silacyclohexyl)-2-fluoro-4'-(2-(4-cyanophenyl)ethyl)biphenyl

Example 39

Trans-4-(4-n-propyl-4-silacyclohexyl)-2-fluoro-4'-(2-(3-fluoro-4-cyanophenyl)ethyl)biphenyl

Example 40

Trans-4-(4-n-pentyl-4-silacyclohexyl)-2-fluoro-4'-(4-cyano-3,5-difluorophenyl)ethyl)biphenyl

Example 41

Preparation of
trans-4-(4-n-propyl-4-silacyclohexyl)-2-fluoro--4'-(2-(4-n-propylphenyl)ethyl)biphenyl An 22-ml tetrahydrofuran solution of 1.05M 4-(2-(4-n-propylphenyl)ethyl)phenyl magnesium bromide was dripped into a mixture of 5.44 g of trans-4-(4-chloro-3-fluorophenyl)-1-n-propyl-1-silacyclohexane, 80 mg of 1,3-bis(diphenylphosphino)propane nickel (II) chloride and 30 ml of tetrahydrofuran, and the resulting mixture was stirred for 20 hours at 50° C. After a conventional after treatment, the reaction mixture was purified by means of silica-gel chromatography to obtain 6.42 g (yield 70%) of the target product.

The following compounds were obtained in the same manner as Example 41.

Example 42

Trans-4-(4-n-propyl-4-silacyclohexyl)-2-fluoro-4'-(2-(3,5-difluoro-4-difluoromethoxyphenyl)ethyl)biphenyl

Example 43

Trans-4-(4-(3-methoxypropyl)-4-silacyclohexyl)-2-fluoro-4'-(2-(3,4-difluorophenyl)ethyl)biphenyl

Example 44

Trans-4-(4-fluoro-4-n-pentyl-4-silacyclohexyl)-4'-(2-(4-chlorophenyl)ethyl)biphenyl

Example 45

Trans-4-(4-n-pentyl-4-silacyclohexyl)-2-fluoro-4'-(2-(3,4-difluorophenyl)ethyl)biphenyl

Example 46

Preparation of
trans-4-(4-n-pentyl-4-silacyclohexyl)-4'-(2-(3,4-4-difluorophenyl)ethyl)biphenyl An 20-ml tetrahydrofuran solution of 1.04M 2-(3,4-difluorophenyl)ethyl zinc chloride was dripped into a mixture of 4.48 g of trans-4-(4-n-pentyl-4-silacyclohexyl)-4'-iodo biphenyl, 80 mg of tetrakis (triphenylphosphine) palladium (0) and 50 ml of toluene, and the resulting mixture was stirred for 10 hours at room temperature. After a conventional after treatment, the reaction mixture was purified by means of silica-gel chromatography to obtain 3.95 g (yield 85%) of the target product.

IR (KBr disc): νmax: 2918, 2108, 1518, 1497, 1288, 1211, 987, 887 and 816 cm$^{-1}$ C-S transition temperature: 59.7° C., S-N transition temperature: 110.0° C., N-I transition temperature: 170.9° C.

The following compounds were obtained in the same manner as Example 46.

Example 47

Trans-4-(1-methyl-4-n-propyl4-silacyclohexyl)-4'-(2-(2-(4-ethyl)biphenyl

Example 48

Trans-4-(4-n-pentyl-4-silacyclohexyl)-2-fluoro-4'-(2-(2-(3-fluoro-4-fluoromethoxyphenyl)ethyl)biphenyl

Example 49

Trans, trans-4-(4-(3-hexenyl)-4-silacyclohexyl)-2-fluoro-4'-(2-(3,4-difluorophenyl)ethyl)biphenyl

Example 50

Trans-4-(4-(3-methylbutyl)-4-silacyclohexyl)-2-fluoro-4'-(2(4-chlorophenyl)ethyl)biphenyl

Example 51

Trans-4-(4-n-propyl-1-silacyclohexyl)-4'-(2-(2,3-difluoro-4-n-propoxyphenyl)ethyl)biphenyl

Example 52

Trans-4-(4-n-pentyl-1-silacyclohexyl)-3'-fluoro-4'-ethyl)biphenyl

Trans-4-(4-(4-fluorobutyl)-4-silacyclohexyl)-4'-(2-(3,4-difluorophenyl)ethyl)biphenyl Example 54

A mixture A comprising 45 mole % of trans-4-(2-(trans-4-(3,4-difluorophenyl)cyclohexyl)ethyl)-1-n-ethyl-1-cyclohexane, 15 mole % of trans-4-(2-(trans-4-(3,4-difluorophenyl)cyclohexyl)ethyl)-1-n-propyl-1-cyclohexane and 40 mole % of trans-4-(2-(trans-4-(3,4-difluorophenyl) cyclohexyl)ethyl)-1-n-pentyl-1-cyclohexane exhibits the following characteristics: $T_{NI}$ (nematic-isotropic transition temperature)=96° C. Δn (anisotropy of the refraction index at 25° C.)=0.0718

A mixture comprising 85 mole % of this mixture A and 15 mole % of the 4-(trans-4-n-pentyl-4-silacyclohexyl)-2-fluoro-4'-(2-(3,4-difluorophenyl)ethyl)biphenyl obtained in Example 30 exhibited an increase in both $T_{NI}$ and Δn. as shown below.

$T_{NI}$=104° C.
Δn=0.0820

Example 55

Preparation of 4-(2-(trans-(4-n-pentyl-4-silacyclohexyl))ethyl)-4'-(4-fluorophenyl)biphenyl 15.1 g (100 mmol) of n-pentyl bromide was dripped into a mixture of 2.4 g of magnesium (100 mmol) and 60 ml of tetrahydrofuran (hereafter referred to as "THF") to obtain a Grignard's reagent. This solution was then dripped into a 300 ml THF solution of 40.9 g of 4-(2-(4-chloro-4-silacyclohexyl)ethyl)-4'-(4-fluorophenyl)biphenyl. The reaction mixture thus obtained was a mixture of trans isomers and cis isomers with respect to the silacyclohexane ring. After a conventional after treatment, they were separated by means of chromatography to obtain 38.1 g (yield 93%) of the target product.

The following compounds were obtained in the same manner as Example 1.

Example 56

4-(2-(trans-(4-n-pentyl-4-silacyclohexyl))ethyl)-4'-(3-fluoro-4-chlorophenyl)biphenyl S-N transition temperature: 208° C.,
N-I transition temperature: 223° C.
IR (KBr disc): vmax: 2914, 2850, 2092, 1481, 1394, 1205, 1076, 889, 833 and 808 cm$^{-1}$ Example 57

4-(2-(trans-(4-n-pentyl-4-fluoro-4-silacyclohexyl))ethyl)-2'-fluoro-4'-(4-cyanophenyl)biphenyl Example 58

Preparation of 4-(2-(trans-(4-n-pentyl-4-silacyclohexyl))ethyl)-4'-(3,4-difluorophenyl)biphenyl 24.9 g (100 mmol) of 4-n-pentyl-4-silacyclohexyl bromide was dripped into a mixture of 2.4 g of magnesium (100 mmol) and 60 ml of THF to obtain a Grignard's reagent. This solution was then dripped into a 300 ml THF solution of 46.4 g of 2(3",4"-difluoroterphenyl)ethyl tosylate and a catalytic amount of dilithium tetrachlorocuprate. The reaction mixture thus obtained was a mixture of trans isomers and cis isomers with respect to the silacyclohexane ring. After a conventional after treatment, they were separated by means of chromatography to obtain 39.4 g (yield 85%) of the target product.

S-N transition temperature: 178° C.,
N-I transition temperature: 185° C.
IR (KBr disc): vmax: 2914, 2854, 2094, 1495, 1184, 966, 887 and 810 cm$^{-1}$ The following compounds were obtained in the same manner as Example 58.

Example 59

4-(2-(trans-(4-methyl-4-n-pentyl-4-silacyclohexyl))ethyl)-4'-(4-cyanobiphenyl)biphenyl Example 60

4-(2-(trans-(4-n-pentyl-4-silacyclohexyl))ethyl)-3-fluoro-4'-(3,5-difluoro-4-difluoromethoxyphenyl)biphenyl Example 61

Preparation of 4-(2-(trans-(4-n-pentyl-4-silacyclohexyl))ethyl)-3'-fluoro-4'-(4-n-propylphenyl)biphenyl 26.3 g (100 mmol) of trans-1-bromomethyl-4-n-pentyl-4-silacyclohexane was dripped into a mixture of 2.4 g of magnesium (100 mmol) and 60 ml of THF to obtain a Grignard's reagent. This solution was then dripped into a 300 ml THF solution of 44.9 g of 4-iodomethyl-3'-fluoro-4"-n-propylterphenyl, 0.5 g of triethyl phosphate and 1 g of cuprous iodide. After a conventional after treatment, the reaction mixture thus obtained was purified by means of chromatography to obtain 43.8 g (yield 90%) of the target product.

C-S transition temperature: 66° C.,
S-N transition temperature: 180° C.,
N-I transition temperature: 210° C.
IR (KBr disc): vmax: 2916, 2848, 2087, 1487, 1298, 1184, 891 and 804 cm$^{-1}$ The following compounds were obtained in the same manner as Example 61.

Example 62

4-(2-(trans-(4-n-pentyl-4-silacyclohexyl))ethyl)-3-fluoro-4'-(4-cyano-3-fluorophenyl)biphenyl Example 63

4-(2-(trans-(4-n-propyl-1-methyl-4-silacyclohexyl))ethyl)-2,3'-difluoro-4'-(4-chlorophenyl)biphenyl Example 64

Preparation of 4-(2-(trans-(4-(3-hexenyl)-4-silacyclohexyl))ethyl)-4'-(3,4-difluorophenyl)biphenyl 24.5 g (100 mmol) of trans-1-(2-chloroethyl)-4-(3-hexenyl)-4-silacyclohexane was dripped into a mixture of 2.4 g of magnesium (100 mmol) and 60 ml of THF to obtain a Grignard's reagent. This solution was then dripped into a 300 ml THF solution of 34.5 g of 4-bromo-3",4"-difluoroterphenyl and a catalytic amount of tetrakis (triphenylphosphine) palladium (0). After a conventional after treatment, the reaction mixture thus obtained was purified by means of chromatography to obtain 39.6 g (yield 87%) of the target product.

The following compounds were obtained in the same manner as Example 64.

Example 65

4-(2-(trans-(4-n-propyl-4-silacyclohexyl))ethyl)-2-fluoro-4'-(4-chlorophenyl)biphenyl

Example 66

4-(2-(trans-(4-n-propyl-4-silacyclohexyl))ethyl)-4'-(3-fluoro-4-trifluoromethoxyphenyl)biphenyl

Example 67

Preparation of 4-(2-(trans-(4-(3-methoxypropyl)-4-silacyclohexyl))ethyl)-4'-(3,4-difluorophenyl)biphenyl 35.5 g (100 mmol) of 4-(2-(trans-(4-(3-methoxypropyl)-4-silacyclohexyl))ethyl)phenyl bromide was dripped into a mixture of 2.4 g of magnesium (100 mmol) and 60 ml of THF to obtain a Grignard's reagent. This solution was then dripped into a 300 ml THF solution of 34.5 g of 4-chloro-3',4'-difluorobiphenyl and a catalytic amount of bis (1,3-diphenylphosphinopropane) nickel (II) chloride. After a conventional after treatment, the reaction mixture thus obtained was purified by means of chromatography to obtain 36.3 g (yield 81%) of the target product.

The following compounds were obtained in the same manner as Example 67.

Example 68

4-(2-(trans-(4-n-pentyl-4-silacyclohexyl))ethyl)-2-fluoro-4'-(4-chloro-3-fluorophenyl)biphenyl

Example 69

4-(2-(trans-(4-(3-hexenyl)-4-silacyclohexyl))ethyl)-2-fluoro-4'-(3,4-difluorophenyl)biphenyl

Example 70

Preparation of 4-(2-(trans-(4-(4-methylpentyl)-4-silacyclohexyl))ethyl)-4'-(3,4-difluorophenyl)biphenyl 26.9 g (100 mmol) of 4-bromo-3',4'-difluorobiphenyl was dripped into a mixture of 2.4 g of magnesium (100 mmol) and 60 ml of THF to obtain a Grignard's reagent. This solution was then dripped into a solution of 50 ml of THF and 13.6 g of zinc chloride to obtain an organozinc reagent. This solution was then dripped into a 300 ml THF solution of 43.7 g of 4(2-(trans-(4-(4-methylpentyl)-4-silacyclohexyl)ethyl)phenyltrifluoromethanesulfonate, catalytic amounts of tetrakis triphenylphosphine palladium and lithium chloride. After a conventional after treatment, the reaction mixture thus obtained was purified by means of chromatography to obtain 41.0 g (yield 86%) of the target product.

The following compounds were obtained in the same manner as Example 70.

Example 71

4-(2-(trans-(4-n-pentyl-4-silacyclohexyl))ethyl)-2-fluoro-4'-(3,4,5-trifluorophenyl)biphenyl

Example 72

4-(2-(trans-(4-n-propyl-1-silacyclohexyl))ethyl)-3'-fluoro-4'-(4-fluorophenyl)biphenyl

Example 73

Preparation of 4-(2-(trans-(4-n-propyl-4-silacyclohexyl))ethyl)-2-fluoro-4'-(3,4-difluorophenyl)biphenyl 19.3 g (100 mmol) of 1-bromo-3,4-difluorobenzene was dripped into a mixture of 2.4 g of magnesium (100 mmol) and 60 ml of THF to obtain a Grignard's reagent. This solution was then dripped into a solution of 50 ml of THF and 13.6 g of zinc chloride t6 obtain an organozinc reagent. This solution was then dripped into a 300 ml THF solution of 49.7 g of 4-(2-(trans-(4-n-propyl-4-silacyclohexyl)ethyl)-2-fluoro-3',4'-difluorobiphenyl and a catalytic amount of tetrakis triphenylphosphine palladium. After a conventional after treatment, the reaction mixture was purified by means of chromatography to obtain 43. 3 g (yield 90%) of the target product.

The following compounds were obtained in the same manner as Example 73.

Example 74

4-(2-(trans-(4-(3-methoxypropyl)-4-silacyclohexyl))ethyl)-2'-fluoro-4'-(3,4-difluorophenyl)biphenyl

Example 75

4-(2-(trans-(4-n-propyl-4-silacyclohexyl))ethyl)-4'-(2,3-difluoro-4-n-propoxyphenyl)biphenyl

Example 76

4-(2-(trans-(4-n-pentyl-4-silacyclohexyl))ethyl)-3'-fluoro-4'-(3,4-difluorophenyl)biphenyl

Example 77

Preparation of trans-4-(2-(4-(4-n-propyl-4-silacyclohexyl)phenyl)ethyl)-3',4'-difluorobiphenyl 2.5 g (20 mmol) of n-propyl bromide was dripped into a mixture of 0.5 g of magnesium (21 mmol) and 50 ml of tetrahydrofuran (hereafter referred to as "THF") to obtain a Grignard's reagent. This solution was then dripped into a 50 ml THF solution of 8.5 g (20 mmol) of 4-(2-(4-chloro-4-silacyclohexyl)phenyl)ethyl-3',4'-difluorobiphenyl to obtain the crude product, which was a mixture of trans isomers and cis isomers with respect to the silacyclohexane ring. After a conventional after treatment, they were separated by means of chromatography to obtain 7. 5 g (yield 86%) of the target product, i.e. the trans isomer.

C-N transition temperature: 63° C.,

N-I transition temperature: 155° C.

IR (KBr disc) vmax: 2914, 2862, 2102, 1605, 1506, 984, 887, 881, 816 and 775 cm$^{-1}$ The following compounds were obtained in the same manner as Example 77.

Example 78

Trans-4-(2-(4-(4-n-propyl-4-silacyclohexyl)phenyl)ethyl)-2,4'-difluorobiphenyl

Example 79

Trans-4-(2-(4-(4-n-propyl-4-silacyclohexyl)phenyl)ethyl)-2,3',4'-trifluorobiphenyl

Example 80

Trans-4-(2-(4-(4-n-propyl-4-silacyclohexyl)phenyl)ethyl)-2-fluoro-4'-n-propylbiphenyl

Example 81

Trans-4-(2-(4-(4-n-pentyl-4-silacyclohexyl)phenyl)ethyl)-2-fluoro-4'-n-chlorobiphenyl

Example 82

Trans-4-(2-(4-(4-n-pentyl-4-silacyclohexyl)phenyl)ethyl)-2-fluoro-4'-n-propoxybiphenyl

Example 83

Trans-4-(2-(4-(4-n-pentyl-4-silacyclohexyl)phenyl)ethyl)-2-fluoro-4'-cyanobiphenyl

Examples 84

Preparation of trans-4-(2-(4-(4-n-pentyl-4-silacyclohexyl)phenyl)ethyl)-3,4'-difluorobiphenyl 5.9 g (20 mmol) of 4-(2-bromoethyl)-3,4'-difluorobiphenyl was dripped into a mixture of 0.5 g of magnesium (21 mmol) and 50 ml of THF to obtain a Grignard's reagent. This solution was then dripped into a 50 ml THF solution of 6.5 g (20 mmol) of 4-(4-n-pentyl-4-silacyclohexyl)-1-bromobenzene and a catalytic amount of tetrakis (triphenylphosphine) palladium (0) to obtain the crude product, which was a mixture of trans isomers and cis isomers with respect to the silacyclohexane ring. After a conventional after treatment, they were separated by means of chromatography to obtain 7.6 g (yield 82%) of the target product, i.e. the trans isomer.

The following compounds were obtained in the same manner as Example 84.

Example 85

Trans-4-(2-(4-(4-(3-methoxypropyl)-4-silacyclohexyl)phenyl)ethyl)-2,3',4'-trifluorobiphenyl

Example 86

Trans-4-(2-(4-(4-(3-pentenyl)-4-silacyclohexyl)phenyl)ethyl)-2-fluoro-4'-n-propylbiphenyl

Examples 87

Preparation of 4-(2-(4-(4-n-pentyl-4-silacyclohexyl)phenyl)ethyl-2',3'-difluoro-4'-n-propoxybiphenyl 6.5 g (20 mmol) of 4-(4-n-pentyl-4-silacyclohexyl)-1-bromobenzene was dripped into a mixture of 0.5 g of magnesium (21 mmol) and 50 ml of THF to obtain a Grignard's reagent. This solution was then dripped into a 50 ml THF solution of 7.1 g (20 mmol) of 4-(2-bromoethyl)-2',3'-difluoro-4'-n-propoxybiphenyl and catalytic amounts of copper (I) iodide and triethylphosphite to obtain the crude product, which was a mixture of trans isomers and cis isomers with respect to the silacyclohexane ring. After a conventional after treatment, they were separated by means of chromatography to obtain 8.3 g (yield 80%) of the target product, i.e. the trans isomer.

The following compounds were obtained in the same manner as Example 87.

Example 88

Trans-4-(2-(4-(4-isobutyl-4-silacyclohexyl)phenyl)ethyl)-2-bromobenzene -fluoro-4'-cyanobiphenyl

Example 89

Trans-4-(2-(4-(4-pentyl-4-methyl-4-silacyclohexyl)phenyl)ethyl)-4'-cyanobiphenyl

Example 90

Preparation of trans-4-(2-(4-(4-n-pentyl-4-silacyclohexyl)phenyl)ethyl)-3',4'-difluorobiphenyl 3.9 g (20 mmol) of 3,4-difluorobromobenzene was dripped into a mixture of 0.5 g of magnesium (20 mmol) and 50 ml of THF to obtain a Grignard's reagent. This solution was then dripped into a solution of 20 ml of THF and 2.8 g (20 mmol) of zinc chloride to obtain an organozinc reagent. This solution was then dripped into a 50 ml THF solution of 8.6 g (20 mmol) of 4-(2-(4-n-pentyl-4-silacyclohexyl)phenyl)ethyl)-1-bromobenzene and a catalytic amount of 1,3-bis(diphenylphosphinopropane) nickel (II) chloride to obtain the crude product, which was a mixture of trans isomers and cis isomers with respect to the silacyclohexane ring. After a conventional after treatment, they were separated by means of chromatography to obtain 8.3 g (yield 90%) of the target product, i.e. the trans isomer.

The following compounds were obtained in the same manner as Example 90.

Example 91

Trans-4-(2-(4-(4-n-propyl-1-silacyclohexyl)phenyl)ethyl)-2,4'-difluorobiphenyl

Example 92

Trans-4-(2-(4-(4-n-pentyl-1-fluoro-1-silacyclohexyl)phenyl)ethyl)-4'-fluorobiphenyl

Example 93

A mixture A comprising 45 % of trans-4-(2-(trans-4-(3,4-difluorophenyl)cyclohexyl)ethyl)-1-n-ethyl-1-cyclohexane, 15 % of trans-4-(2-(trans-4-(3,4-difluorophenyl)cyclohexyl)ethyl)-1-n-propyl-1-cyclohexane and 40 % of trans-4-(2-(trans-4-(3, 4-difluorophenyl)cyclohexyl)ethyl)-1-n-pentyl-1-cyclohexane exhibits the following characteristics:

$T_{NI}$ (nematic-isotropic transition temperature)=96° C.

$T_{CN}$ (crystal-nematic transition temperature)=10° C.

$\Delta n$ (anisotropy of the refraction index at 25° C.)=0.0718

A mixture comprising 85% of this mixture A and 15% of the trans-4-(2-(4-(4-n-propyl-4-silacyclohexyl)phenyl)ethyl)-3',4'-difluorobiphenyl obtained in Example 77 exhibited an increase in both $T_{NI}$ and $\Delta n$ as well as a decrease in $T_{CN}$, as shown below.

$T_{NI}$=103° C.

$T_{CN}$=−16° C.

$\Delta n$=0.0864

As described thus far, the compound of this invention provides a conventionally unknown and completely new liquid crystal compound containing silacyclohexane rings with a silicon atom(s) in its molecular structure which has both a high and a large Δn. Since it has a high $T_{NI}$, the liquid crystal range is extended to a high temperature region and therefore it is excellent, for example, for a liquid crystal panel composition for automobile onboard use. Also, because of a large Δn, the response time can be shortened, for example, in the STN (super twisted nematic) mode, and the contrast can be improved in the PDLC (polymer dispersion liquid crystal) mode and the PNLC (polymer network liquid crystal) mode.

We claim:

1. A silacyclohexane compound represented by the following general formula (I)

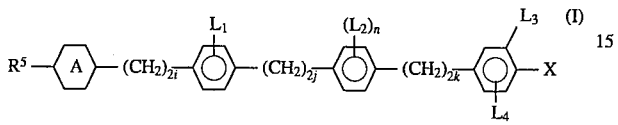

wherein, R denotes a linear-chain alkyl group with 1–10 carbon atoms, a fluoralkyl group with 1–10 carbon atoms in which a fluorine atom(s) is substituted for one or two hydrogen atoms, a branched-chain alkyl group with 3–8 carbon atoms, an alkoxyalkyl group with 2–7 carbon atoms, or an alkenyl group with 2–8 carbon atoms;

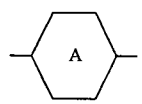

denotes a trans-1-sila-1,4-cyclohexylene or trans-4-sila-1,4-cyclohexylene group whose silicon at position 1 or position 4 has a substitutional group(s) of H, F, Cl or $CH_3$;

$L_1$ and $L_2$ independently denote H or F;

$L_3$ and $L_4$ independently denote H, F or Cl;

X denotes a H, CN, F, Cl, $CF_3$, $CF_2Cl$, $CHFCl$, $OCF_3$, $OCF_2Cl$, $OCHFCl$, $OCHF_2$, or a linear-chain alkyl or alkoxy group with 1–10 carbon atoms; and i, j and k respectively denote 0 or 1, where (i+j+k) is 0 or 1, n denotes 0, 1 or 2.

2. A method of preparing the silacyclohexane compound as described in claim 1 comprising carrying out a reaction selected from a carbon-silicon bond formation reaction and a carbon-carbon bond formation reaction including a reduction reaction between an organometallic reagent

R—M (M denotes MgP (P denotes a halogen atom), ZnP or Li), and a silacyclohexane compound

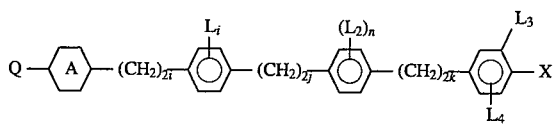

wherein Q denotes a halogen atom, or an alkoxy, methansulfonyloxy, benzenesulfonyloxy, p-toluenesulfonyloxy or perfluoroalkanesulfonyloxy group.

3. A method of preparing the silacyclohexane compound as described in claim 1 comprising carrying out a carbon-carbon bond formation reaction including a reduction reaction between an organometallic reagent

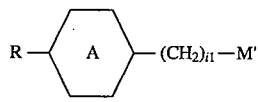

(M' denotes M or $B(OY)_2$ M denotes MqP (P denotes a halogen atom), Zn or Li (Y denotes H or an alkyl group) and a compound

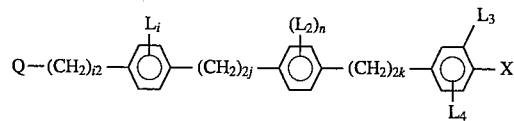

wherein Q denotes a halogen atom, or alkoxy, methanesulfonyloxy, benzeneslfonyloxy, p-toluenesulfanyloxy or perfluoroalkanesulfonyloxy group, i1 and i2 respectively denote 0, 1 or 2 where (i1+i2) is 0 or 2, and j and k respectively denote 0 or 1 where {(i1+i2)+2j+2k} is 0 or 2.

4. A method of preparing the silacyclohexane compound as described in claim 1 comprising carrying out a carbon-carbon bond formation reaction including a reduction reaction between an organometallic reagent

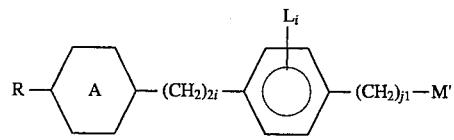

wherein M' denotes M or $B(OY)_2$, M denotes MqP (P denotes a halogen atom, Zn or Li (Y denotes H or an alkyl group), and a compound

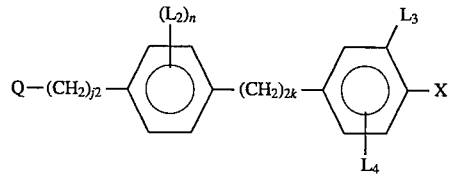

wherein Q denotes a halogen atom, or an alkoxy, methanesulfonyloxy, benzenesulfonyloxy, p-toluenesulfonyoxy or. perfluoroalkanesulfonyloxy group, wherein j1 and j2 respectively denote 0, 1 or 2 where (j1+j2) is 0 or 2, and i and k respectively denote 0 or 1 where {2i+(j1+j2)+2k} is 0 or 2.

5. A method of preparing the silacyclohexane compound as described in claim 1 comprising carrying out a carbon-carbon bond formation reaction including a reduction reaction between a silacyclohexane compound

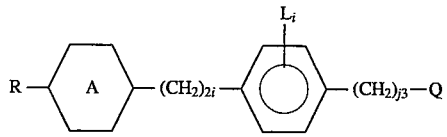

wherein Q denotes a halogen atom, or an alkoxy, methanesulfonyloxy, benzenesulfonyloxy, p-toluenesulfonyloxy or perfluoroalkanesulfonyloxy group, and an organometallic reagent

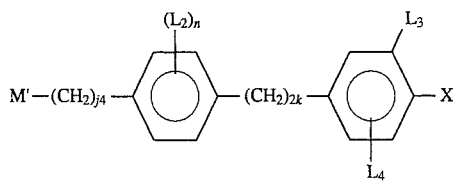

wherein (M' denotes M or B(OY)$_2$ M denotes MgP (P denotes a halogen atom), Zn Or Li (Y denotes H or an alkyl group) j3 and j4 respectively denote 0, 1 or 2 where (j3+j4) is 0 or 2, and i and k respectively denote 0 or 1 where {2i+(j3+j4)+2k} is 0 or 2.

6. A method of preparing the silacyclohexane compound as described in claim 1 comprising carrying out a carbon-carbon bond formation reaction including a reduction reaction between a silacyclohexane compound

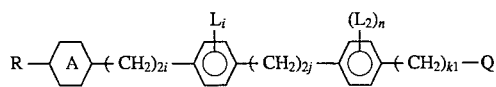

wherein Q denotes a halogen atom, or an alkoxy, methanesulfonyloxy, benzenesulfonyloxy, p-toluenesulfonyloxy or perfluoroalkanesulfonyloxy group, and an organometallic reagent

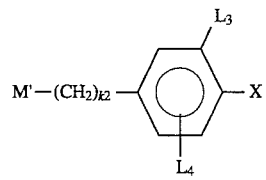

wherein M' denotes M or B(,OY)$_2$, M denotes MgP (P denotes a halogen atom), Zn or Li (Y denotes H or an alkyl group), k1 and k2 respectively denote 0, 1 or 2 where (k1+k2) is 0 or 2, and i and j respectively denote 0 or 1 where {2i+2j+(k1+k2)} is 0 or 2.

7. A liquid crystal composition comprising the silacyclohexane compound of claim 1.

8. A liquid crystal display element comprising the liquid crystal composition of claim 7.

9. A silacyclohexane compound represented by the following general formula (II)

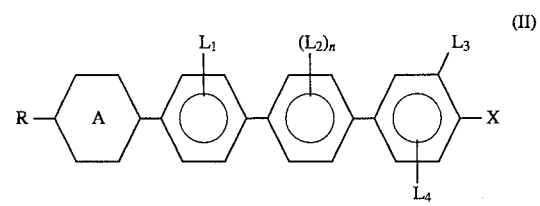

wherein, R denotes a linear-chain alkyl group with a carbon number of 1–10, a fluoroalkyl group with a carbon number of 1–10 in which a fluorine atom(s) is substituted for one or two hydrogen atoms, a branched-chain alkyl group with a carbon number of 3–8, an alkoxyalkyl group with a carbon number of 2–7, or an alkenyl group with a carbon number of 2–8;

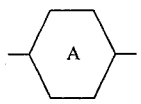

denotes a trans-1-sila-1,4-cyclohexylene or trans-4-sila-1,4-cyclohexylene group whose silicon at position 1 or position 4 has a substitutional group(s) of H, F, Cl or CH$_3$;

L$_1$, and L$_2$ independently denote H or F;

L$_3$ and L$_4$ independently denote H, F or Cl;

X denotes a H, CN, F, Cl, CF$_3$, CF$_2$Cl, CHFCl, OCF$_3$, OCF$_2$ Cl, OCHFCl, OCHF$_2$, or a linear-chain alkyl or alkoxy group with a carbon number of 1–10; and n denotes 0, 1 or 2.

10. A silacyclohexane compound represented by the following general formula (III)

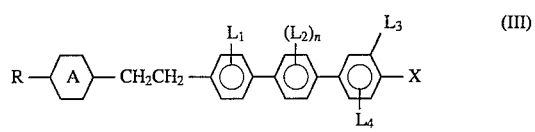

wherein, R denotes a linear-chain alkyl group with a carbon number of 1–10, a fluoroalkyl group with a carbon number of 1–10 in which a fluorine atom(s) is substituted for one or two hydrogen atoms, a branched-chain alkyl group with a carbon number of 3–8, an alkoxyalkyl group with a carbon number of 2–7, or an alkenyl group with a carbon number of 2–8;

denotes a trans-1-sila-1,4-cyclohexylene or trans-4-sila-1,4-cyclohexylene group whose silicon at position 1 or position 4 has a substitutional group(s) of H, F, Cl or CH$_3$;

L$_1$ and L$_2$ independently denote H or F;

L$_3$ and L$_4$ independently denote H, F or Cl; X denotes a H, CN, F, Cl, CF$_3$, CF$_2$Cl, CHFCl, OCF$_3$, OCF$_2$ Cl, OCHFCl, OCHF$_2$, or a linear-chain alkyl or alkoxy group with a carbon number of 1–10; and n denotes 0, 1 or 2.

11. A silacyclohexane compound represented by the following general formula (IV)

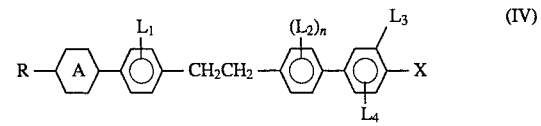

wherein, R denotes a linear-chain alkyl group with a carbon number of 1–10, a fluoroalkyl group with a carbon number of 1–10 in which a fluorine atom(s) is substituted for one or two hydrogen atoms, a branched-chain alkyl group with a carbon number of 3–8, an alkoxyalkyl group with a carbon number of 2–7, or an alkenyl group with a carbon number of 2–8;

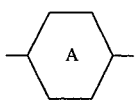

denotes a trans-1-sila-1,4-cyclohexylene or trans-4-sila-1,4-cyclohexylene group whose silicon at position 1 or position 4 has a substitutional group(s) of H, F, Cl or $CH_3$;

$L_1$ and $L_2$ independently denote H or F;

$L_3$ and $L_4$ independently denote H, F or Cl;

X denotes a H, CN, F, Cl, $CF_3$, $CF_2Cl$, $CHFCl$, $OCF_3$, $OCF_2Cl$, $OCHFCl$, $OCHF_2$, or a linear-chain alkyl or alkoxy group with a carbon number of 1–10; and n denotes 0, 1 or 2.

12. A silacyclohexane compound represented by the following general formula (V)

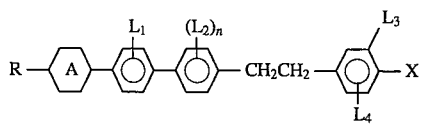 (V)

wherein, R denotes a linear-chain alkyl group with a carbon number of 1–10, a fluoroalkyl group with a carbon number of 1–10 in which a fluorine atom(s) is substituted for one or two hydrogen atoms, a branched-chain alkyl group with a carbon number of 3–8, an alkoxyalkyl group with a carbon number of 2–7, or an alkenyl group with a carbon number of 2–8;

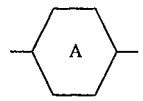

denotes a trans-1-sila-1,4-cyclohexylene or trans-4-sila-1,4-cyclohexylene group whose silicon at position 1 or position 4 has a substitutional group(s) of H, F, Cl or $CH_3$;

$L_1$ and $L_2$ independently denote H or F;

$L_3$ and $L_4$ independently denote H, F or Cl;

X denotes a H, CN, F, Cl, $CF_3$, $CF_2Cl$, $CHFCl$, $OCF_3$, $OCF_2Cl$, $OCHFCl$, $OCHF_2$, or a linear-chain alkyl or alkoxy group with a carbon number of 1–10; and n denotes 0, 1 or 2.

* * * * *